United States Patent

Turner et al.

[11] Patent Number: 5,961,942
[45] Date of Patent: Oct. 5, 1999

[54] EFFLUENT GAS TREATMENT

[75] Inventors: John Arthur Turner, North Yorkshire; Ian Charles Jeffery, Cleveland, both of United Kingdom

[73] Assignee: E. I. du Pont de Nemours and Company, Wilmington, Del.

[21] Appl. No.: 08/985,668

[22] Filed: Dec. 5, 1997

Related U.S. Application Data

[63] Continuation of application No. PCT/GB96/01261, May 28, 1996.

[30] Foreign Application Priority Data

| Jun. 5, 1995 | [GB] | United Kingdom | 9511275 |
| Jan. 25, 1996 | [GB] | United Kingdom | 9601493 |
| Feb. 1, 1996 | [GB] | United Kingdom | 9602050 |
| Feb. 7, 1996 | [GB] | United Kingdom | 9602458 |

[51] Int. Cl.⁶ .............................. C01B 7/09; B01D 53/70
[52] U.S. Cl. .................................. 423/240 S; 423/245.3; 423/502; 423/488
[58] Field of Search .................. 423/240 S, 245.3, 423/488, 500, 502; 562/416

[56] References Cited

U.S. PATENT DOCUMENTS

| 3,731,485 | 5/1973 | Rudolph et al. | 60/39.05 |
| 4,537,023 | 8/1985 | Nakamura et al. | 60/39.05 |
| 4,610,137 | 9/1986 | Nakamura et al. | 60/39.511 |
| 4,722,190 | 2/1988 | Yamamoto et al. | 60/648 |
| 5,612,007 | 3/1997 | Abrams | 422/189 |
| 5,614,159 | 3/1997 | Modic et al. | 423/245.3 |
| 5,643,545 | 7/1997 | Chen et al. | 423/240 S |

FOREIGN PATENT DOCUMENTS

| 0 013 100 | 7/1980 | European Pat. Off. |
| 0 031 200 | 7/1981 | European Pat. Off. |
| 51487 | 5/1982 | European Pat. Off. |
| 0 485 787 | 5/1992 | European Pat. Off. |
| 0 498 591 | 8/1992 | European Pat. Off. |
| 0 502 628 | 9/1992 | European Pat. Off. |
| 0 504 937 | 9/1992 | European Pat. Off. |
| 0 547 226 | 7/1993 | European Pat. Off. |
| 0 664 148 | 7/1995 | European Pat. Off. |
| 51-131458 | 11/1976 | Japan . |
| 55-099517 | 7/1980 | Japan . |
| 56-040636 | 4/1981 | Japan . |
| 56-072221 | 7/1981 | Japan . |
| 60-048615 | 10/1985 | Japan . |
| 61-106924 | 5/1986 | Japan . |
| 86-052728 | 11/1986 | Japan . |
| 92-068453 | 11/1992 | Japan . |
| 5-23598 | 2/1993 | Japan | 423/240 S |
| 5-337373 | 12/1993 | Japan | 423/240 S |
| 08-155265 | 6/1996 | Japan . |
| 916380 | 3/1982 | U.S.S.R. | 423/241 |
| 93/24440 | 12/1993 | WIPO . |
| 96/11899 | 4/1996 | WIPO . |

OTHER PUBLICATIONS

Article entitled First Large Scale Catalytic Oxidation System for PTA plant CO and VOC Abatement: by T G Otchy and K J Herbert (presented at 85th Annual Meeting and Exhibition fo Air Association Management Association) Jun. 1992.

Article entitled "Amoco marks Belgian first" in Process Technology journal (Jul. 1992).

*Primary Examiner*—Ngoc-Yen Nguyen
*Attorney, Agent, or Firm*—Charles E. Krukiel

[57] ABSTRACT

Process for removing organic constituents from a high pressure exhaust gas stream in a bromine assisted air oxidation process in which the exhaust gas contains methyl bromide.

2 Claims, 1 Drawing Sheet

EFFLUENT GAS TREATMENT

CROSS-REFERENCE TO RELATED APPLICATIONS

The application is a continuation of PCT/GB96/01261 filed May 28, 1996, which in turn claims foreign priority benefit of GB Application 9511275.1, filed Jun. 5, 1995; GB Application 9601493.1, filed Jan. 25, 1996; GB Application 9602050.8, filed Feb. 1, 1996; and GB Application 9602458.3, filed Feb. 7, 1996.

BACKGROUND OF THE INVENTION

This invention relates to effluent gas treatment, especially treatment of effluent gases obtained from the production of aromatic carboxylic acids such as terepthalic acid.

The invention has application for example to the catalytic combustion of a high pressure effluent gas stream containing combustible components.

In a known process, disclosed in Japanese Kokai 55-99517, for use in the production of terephthalic acid an effluent gas containing combustible and corrosive components such as acetic acid, methyl acetate, p-xylene and carbon monoxide is subjected to catalytic combustion while still at high pressure and the treated gas is then passed through a gas turbine to recover energy which can then be used elsewhere in the terephthalic acid production process. The known method is said to render all combustible and corrosive components of the effluent gas innocuous and the treated gas is exhausted to atmosphere.

Significantly, JP-A-55-9517 makes no reference to any bromine constituent in the effluent gas. However, a commonly used process for the production of terephthalic acid involves the liquid phase oxidation of p-xylene in a carboxylic acid solvent such as acetic acid in the presence of a heavy metal catalyst system including a bromine constituent as a promoter. Where bromine is present, the high pressure effluent gas obtained from the oxidation reaction will contain bromine, mainly in the form of methyl bromide. Methyl bromide is toxic and, if discharged into the atmosphere, is believed to deplete atmospheric ozone. It is therefore important to avoid discharge of methyl bromide into the atmosphere.

If a scheme such as that disclosed in JP-A-55-99517 is used to treat effluent gas containing methyl bromide, the catalytic oxidation will be effective to convert at least some of the methyl bromide into bromine and hydrogen bromide (HBr), components which are potential corrosion-producing agents especially if expensive corrosion resistant materials are to be avoided for fabrication of equipment downstream of the catalytic oxidation zone. The absence of any reference to methyl bromide in JP-A-55-99517 suggests that the terephthalic acid production route either did not employ bromine as a catalyst component or else involved some form of removal system prior to catalytic oxidation or the use of expensive corrosion resistant materials for the construction of equipment handling the effluent gas.

It is believed that in a process already in use bromine and HBr resulting from the catalytic oxidation of effluent gas stream containing, inter alia, methyl bromide are eliminated prior to passage of the treated gas through a gas turbine by scrubbing the pressurised treated gas stream to remove these components. Whilst this is an effective way of ensuring that the materials used in the fabrication of the gas turbine are not exposed to the corrosive bromine components from the gas, the step of scrubbing the gas stream is inevitably accompanied by reduction in the temperature and pressure of the treated gas stream. Consequently, the energy recoverable from the gas stream is reduced.

SUMMARY OF THE INVENTION

According to the present invention there is provided a process for the treatment of an effluent gas stream, comprising subjecting the effluent gas while at elevated pressure to catalytic combustion and passing the treated gas to an energy recovery system, characterised in that:

the effluent gas stream contains a first bromine compound or compounds convertible on catalytic combustion into a further gaseous bromine compound or compounds which, in the liquid phase, are corrosive with respect to the materials from which the energy recovery system is fabricated;

the effluent gas stream containing said first bromine compound(s) is subjected to catalytic combustion;

the treated gas containing said further gaseous bromine compound(s) is passed to the energy recovery system;

pressure and temperature conditions are controlled so as to prevent condensation of said further bromine compound(s) on passage through the energy recovery system; and following passage through the energy recovery system, said further bromine compound(s) are removed from the treated gas.

Thus, instead of removing the potentially corrosive bromine compounds prior to passage of the treated gas stream through the energy recovery system eg by scrubbing the gas stream, in accordance with the invention the temperature of the treated gas stream is maintained and corrosion is suppressed by control of the temperature and pressure conditions to ensure the potentially corrosive bromine compound (s) remain in the gaseous phase during passage through the energy recovery system. In this way, full advantage is taken of the high temperature imparted to the gas stream in the course of catalytic combustion without the necessity of fabricating the energy recovery system using expensive highly corrosion-resistant materials. Thus, for example, the energy recovery system (eg a gas turbine) may be fabricated using more conventional materials such as high chrome or austenitic stainless steels.

The process of the invention is particularly applicable to treatment of an effluent gas in which said first bromine compound comprises methyl bromide and in which catalytic combustion of the methyl bromide results in the production of bromine and/or HBr as said further bromine compound (s).

DETAILED DESCRIPTION OF THE INVENTION

Figure 1:
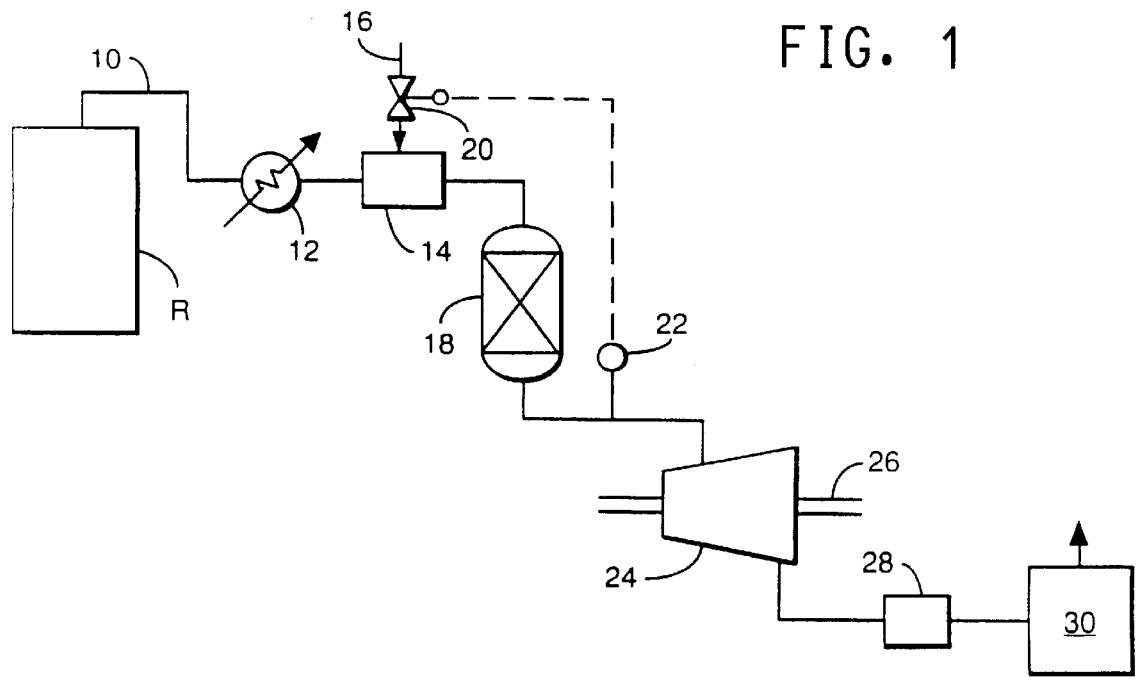
FIG. 1 is a schematic flow diagram illustrating one embodiment of the invention as applied to the treatment of an effluent gas stream derived from plant for the production of terephthalic acid.

The invention has particular application to the treatment of effluent gas derived from the production of an aromatic polycarboxylic acid such as terephthalic acid by means of liquid phase oxidation of a suitable precursor (i.e. p-xylene in the case of terephthalic acid) in an aliphatic carboxylic acid solvent such as acetic acid in the presence of a catalyst system including a source of bromine such as hydrogen bromide, the catalyst usually comprising heavy metal compounds such as compounds of cobalt and manganese. The process may be as disclosed for example in our prior EP-A-498591 and EP-A-502628, the entire disclosures of which are incorporated herein by this reference.

The effluent gas stream in this case is derived from the overheads vapour withdrawn from the oxidation reactor, the overheads vapour being processed to remove a substantial proportion of the acetic acid, leaving a gaseous effluent gas stream comprising, inter alia, organics such as methyl bromide, acetic acid, methyl acetate, paraxylene and benzene, together with nitrogen, water vapour, carbon monoxide, carbon dioxide and oxygen. The gaseous effluent stream is processed in accordance with the process of the present invention to eliminate substantially all of the organic constituents.

Typically the effluent gas stream is at a pressure in the range of 5 to 25 bara (for instance between 10 and 16 bara) and a temperature of the order of 40° C. Prior to catalytic combustion the effluent gas stream is conveniently heated (eg by means of high pressure steam, heating oil, heat exchange between the untreated and the treated gas stream, passage through a fuel-fired heater or by direct firing of fuel into the gas stream) to an elevated temperature, usually in the range of 250 to 400° C. (typically about 300° C.).

Depending on the exotherm available from the catalytic combustion step, it may be appropriate to introduce a combustion assistant into the catalytic combustion zone. The combustion assistant is preferably pre-mixed with the gas stream prior to entry into the combustion zone. One form of device for effecting good mixing of the combustion assistant with the gas stream is disclosed in our prior PCT Published Patent Application No. WO 94/23813, the disclosure of which is incorporated herein by this reference.

The combustion assistant is preferably, but need not necessarily be, one including oxygen. Various assistants may be used, eg methanol, methyl acetate, hydrogen, natural gas, methane, propane, butane or mixtures thereof. Where methyl acetate is used, it is conveniently derived from the terephthalic acid production process as it is generated as a by-product of the liquid phase oxidation of p-xylene in acetic acid solvent. Where methane is used, it may be derived from an anaerobic process for the treatment of effluent produced in the manufacture of the aromatic carboxylic acid, e.g. terephthalic acid. If desired, additional air may be introduced into the catalytic combustion zone to promote oxidation.

The catalytic combustion is carried out with regard to ensuring that, during the subsequent expansion on passage through the energy recovery system, bromine and HBr derived from the methyl bromide constituent of the effluent gas stream remain in the gas phase thereby avoiding dew point corrosion conditions in the energy recovery system. Usually the temperature of the exiting gas stream will be in the range from about 250 to about 700° C., e.g. 350 to 700° C., and will depend on whether or not the gas stream is preheated before introduction into the catalytic combustion zone and whether or not a combustion assistant is employed. For instance, the catalytic combustion may be conducted in such a way that the temperature of the treated gas exiting the catalytic combustion zone is of the order of 400° C. or greater. Where no combustion assistant is used, or where the combustion assistant is one which is easily or relatively easily oxidised (e.g. methanol, methyl acetate or hydrogen) the exit temperature may be in the range of about 250 to about 550° C., typically about 350 to 500° C. (e.g. about 480° C.). With a combustion assistant which is less readily oxidisable (e.g. methane, propane or butane) the exit temperature will usually be higher, i.e. about 400 to about 700° C., typically 550 to 700° C., e.g. of the order of 630° C.

In general, the catalytic combustion process will be carried out using operating conditions (eg. temperature, space velocity, catalyst composition) selected to ensure that methyl bromide is substantially completely converted to HBr and $Br_2$, the aim being to minimise or avoid the production of underconversion brominated aromatic compounds which have high dew points. In addition, pressure and temperature conditions are controlled so as to prevent condensation of the HBr and/or $Br_2$ compound(s) on passage through the energy recovery system.

The energy recovery system may produce an output in mechanical or electrical form and may for instance be used to power other equipment in the production plant such as a compressor forming part of the system for feeding air, oxygen-enriched air, oxygen-containing gas or oxygen to the reactor in which the liquid phase oxidation is carried out.

According to a further aspect of the present invention there is provided in a process for the production of a polycarboxylic acid such as terephthalic acid, which process comprises oxidising a precursor of said polycarboxylic acid (e.g. paraxylene) in a reaction medium comprising an aliphatic carboxylic acid (e.g. acetic acid) to produce a slurry of crude terephthalic acid in said aliphatic acid, and replacing the aliphatic carboxylic acid in said slurry with water to produce a wet deposit of crude polycarboxylic acid containing water for use in the subsequent purification of the crude polycarboxylic acid (e.g. by hydrogenation of an aqueous solution formed from said wet deposit), replacement of the aliphatic carboxylic acid with water being effected by means of an integrated separation and water washing filter operating under elevated pressure conditions, the steps of catalytically combusting methyl bromide-containing gaseous effluent derived from the oxidation reaction under elevated pressure conditions, optionally in the presence of a combustion assistant, to effect conversion to bromine and/or hydrogen bromide, passing the treated gas containing bromine and/or HBr in the vapour phase through an energy recovery system under temperature and pressure conditions such that condensation of the bromine and/or HBr is substantially prevented; and removing the bromine and/or HBr from the treated gas following passage through the energy recovery system.

The integrated separation and water washing filter may comprise a gas pressurised belt filter, a gas pressurised rotary cylindrical filter or a hydraulically pressurised multi-celled pressure drum filter. In each instance, the washing operation may be carried out in stages, preferably in countercurrent fashion so that the filter cake is washed with water of increasing purity as it advances downstream from the location at which separation of the crystals from the mother liquor takes place.

Typically the filter operates with a pressure differential in the range of 0.1 to 15 bara (preferably between 0.3 and 7 bara), preferably such that the pressure on the lower pressure side thereof is no less than one bara although we do not exclude the possibility of the lower pressure side being at sub-atmospheric pressure.

Another aspect of the invention is concerned with the removal from the gas stream of bromine and/or hydrogen bromide following catalytic combustion, particularly with the aim of processing the gas stream to remove the bromine components so that any discharge to atmosphere is substantially free of such components. Although this aspect of the invention is applicable to scrubbing of the gas stream following passage through the energy recovery system, it is also applicable to scrubbing of the gas stream upstream of the energy recovery system in circumstances where this is desired. Such processing may for instance be effected by desuperheating the gas stream using water and contacting the gas stream with a suitable aqueous scrubbing media in a scrubbing section to remove the $Br_2$ and HBr. HBr for instance may be removed by countercurrent contact with HBr solution or it may be removed simply by contact with water, e.g. a water spray, while at the same time desuperheating the treated gas. Contacting the treated gas with HBr solution is for instance appropriate where the aim is to recover HBr for reuse as part of the catalyst system employed in the oxidation reactor. Where this is not required, water may be used. If used, it is preferred that sufficient water is employed to irrigate the pipeline transporting the water treated gas downstream and thereby prevent corrosion problems. $Br_2$ may be removed by countercurrent contact with an aqueous solution of components such as sodium hydroxide, sodium carbonate, sodium bicarbonate, sodium bromide, sodium formate, sodium sulphite or mixtures containing any combination of two or more of these compounds (e.g. sodium hydroxide and sodium sulphite).

A further aspect of the invention is concerned with the supply of combustion assistant to the catalytic combustion of the effluent gas stream. According to this aspect of the invention there is provided a process for the production of aromatic carboxylic acids comprising:

a) oxidising an aromatic precursor to the aromatic carboxylic acid in a lower aliphatic monocarboxylic acid by means of an oxidising agent in the presence of water and a heavy metal oxidation catalyst system including a bromine compound or compounds, resulting in the production of a high pressure effluent vapour stream containing water, gaseous components and organic components including said aliphatic acid and methyl bromide;

b) reducing said aliphatic acid content of the effluent vapour stream to derive a high pressure offgas stream comprising water, gaseous components and organic components including said aliphatic acid and methyl bromide;

c) catalytically combusting the high pressure offgas stream in such a way as to convert substantially all of the methyl bromide content to bromine and/or hydrogen bromide, the catalytic combustion being carried out in the presence of an organic combustion assistant constituted by a by-product from the plant for production of the aromatic acid; and d) passing the combusted oxidised gas stream through an energy recovery system.

Thus, in this aspect of the invention, the combustion assistant is derived from the process for the production of the aromatic carboxylic acid and may be for instance methyl acetate recovered from the vapour stream produced in the course of the oxidation reaction or it may be methane produced in an anaerobic waste treatment process forming part of the overall process for the production of the aromatic acid.

In this aspect of the invention, scrubbing of the combusted gas stream to remove the bromine and/or hydrogen bromide components may be carried out using any one or more of the scrubbing agents and techniques described above and may be carried out prior to, or subsequent to, passage of the gas stream through the energy recovery system.

Referring to FIG. 1, the effluent gas stream entering the treatment plant via line 10 is derived from the overheads condensing and scrubbing system associated with a reactor R for the production of terephthalic acid by liquid phase oxidation of p-xylene, for example by means of the process disclosed in our prior EP-A-498591 and/or EP-A-502628.

In the process disclosed in these patent applications, catalysed liquid phase oxidation of paraxylene is carried out in a solvent comprising aceticacid to produce terephthalic acid, the catalyst system comprising heavy metals such as cobalt and manganese and bromine promoter. The temperature of the liquid phase reaction is controlled by withdrawing a vapour phase overheads stream from the reactor comprising the aliphatic acid, water, gaseous by-products including methyl bromide and methyl acetate, and gases such as nitrogen, carbon monoxide, carbon dioxide and oxygen. Following processing involving removal of a large proportion of the acetic acid, an offgas or gaseous effluent stream is obtained which is at elevated pressure. Processing of the overheads stream typically comprises passing the stream to a condensing system to produce an aqueous condensate containing acetic acid and said offgas or gaseous effluent stream. A proportion of the aqueous condensate is supplied to a distillation column in which water is separated from acetic acid to produce a water-rich top product and an acetic acid-rich bottom product which is recycled to the oxidation reactor. The remainder of the aqueous condensate may be refluxed to the reactor R. The water-rich top product obtained from distillation provides a source of water for use in the manner disclosed in EP-A-498591 and EP-A-502628.

A feature of the process disclosed in EP-A-498591 and EP-A-502628 is the handling of the aqueous mother liquor produced in the purification process. The purification process involves the hydrogenation of an aqueous solution of crude terephthalic acid obtained from the oxidation of paraxylene, crystallisation of purified terephthalic acid and separation of the purified crystals from the aqueous mother liquor. The resulting mother liquor contains impurities such as paratoluic acid and in prior processes was treated as a waste. EP-A-498591 and EP-A-502628 teach recycle of at least part of this primary mother liquor by treating it (by cooling or evaporation) to precipitate further, but less pure, terephthalic acid and feeding the resulting secondary mother liquor (as a reflux feed) to the distillation column for separating water and acetic acid in such a way that high boiling point impurities such as paratoluic acid are recovered in the acetic acid-rich bottom product withdrawn from the column for recycle to the oxidation reactor. The less pure terephthalic acid precipitate is also recycled to the oxidation reactor, e.g. by slurrying it in acetic acid derived from the distillation column.

The effluent treatment disclosed herein may for instance be used In conjunction with aromatic polycarboxylic acid production plant wherein the crude acid crystals and the purified acid crystals are separated from the primarily aliphatic carboxylic acid mother liquor and primarily aqueous mother liquor respectively and are subjected to washing with water by means of an integrated solids separation and water washing apparatus such as those described in our prior published International Patent Applications Nos. WO 93/24440 and WO 94/17982 (the entire disclosures of which are incorporated herein by this reference) so that the mother liquor is replaced by water as a result of washing. Thus, for example the integrated solids separation and water washing apparatus may comprise a belt filter unit operated with the slurry side under superatmospheric conditions, or a pressurised rotary cylindrical filter unit operated with the slurry side under superatmospheric conditions, or a pressure drum filter unit (e.g. a BHS-Fest pressure filter drum formed with a plurality of slurry receiving cells in which the mother liquor is displaced from filter cake by water under hydraulic pressure supplied to the cells).

The effluent gas stream is typically at a pressure of the order of 10 to 16 bara and a temperature of the order of 40° C. and typically contains, inter alia, volatile organics such as methyl bromide, acetic acid and benzene, together with nitrogen, water vapour, carbon monoxide, carbon dioxide and oxygen. A typical composition (expressed in terms of molar percent) is as follows:

| | |
|---|---|
| Nitrogen | 94.5 |
| Oxygen | 3.0 |
| Carbon monoxide | 0.45 |
| Carbon dioxide | 1.35 |
| Water | 0.5 |
| Organics | 0.2 | where the organics component includes acetic acid, methyl acetate, methanol, benzene, toluene, paraxylene and methyl bromide, the latter compound typically being present in an amount of about 50 ppm relative to the total gas stream.

The gas stream is preheated in heat exchanger 12 using high pressure steam as the heat source. Typically the temperature of the gas stream following such heat exchange is of the order of 250 to 300° C. The gas stream then enters a mixer 14 into which a combustion assistant is also introduced via line 16, the combined gas stream and combustion assistant then being fed to a catalytic combustion unit 18 with a space velocity of the order of $10^3$ to $5 \times 10^4 h^{-1}$, preferably $5 \times 10^3$ to $2 \times 10^4\ h^{-1}$.

A convenient combustion assistant is methyl acetate which is produced as a by-product in the terephthalic acid production process. Various other combustion assistants may be used instead or in addition, especially those which contain oxygen —eg methanol. The amount of combustion assistant introduced is such that the temperature of the combusted gas stream exiting the catalytic combustion unit 18 is of the order of 400° C. or greater, typically of the order of 480° C. A feedback arrangement comprising valve 20 in line 16, temperature sensor 22 and appropriate control equipment is used to regulate the supply of combustion assistant to the mixer 14 so that the desired temperature is maintained at the exit of the unit 18.

The catalyst employed in the catalytic combustion unit 18 may comprise any suitable oxidation catalyst to secure substantially total conversion of methyl bromide to bromine and HBr while also securing, in combination with the combustion assistant (where needed), substantially total oxidation of other organics such as acetic acid and production of heat to produce the desired exit temperature. Typically the catalyst employed comprises a noble metal catalyst such as platinum and/or palladium supported on an inert support. The support may be ceramic or metallic in the form of a monolith or pellets. Suitable commercial catalysts are available from catalyst manufacturers such as Johnson Matthey (e.g. Halocat AH/HTB-10 catalyst), Allied Signal/Degussa (e.g. HDC-2 or T2-HDC catalyst) and Engelhard (e.g. VOCAT 300H or VOCAT 450H catalyst).

Following catalytic combustion, the treated gas stream typically has a temperature of the order of 400 to 700° C. and a pressure only marginally lower than the untreated gas stream, ie about 9.5 to 15.5 bara in the case where the untreated gas stream has a pressure of the order of 10 to 16 bara. The treated gas is then passed through expander 24 in which the energy content of the gas stream is converted into mechanical power which, via shaft 26, can be employed appropriately within the terephthalic acid production process, for instance as power input for an air compressor for feeding air under pressure to the oxidation reactor of the production process or for generation of electric power for distribution either within the plant or to other users. At the exit side of the expander 24, the gas stream temperature is typically of the order of 140 to 200° C. (eg about 170° C.) and its pressure is near atmospheric, eg about 1.2 bara. The temperature and pressure conditions employed are such that the bromine and HBr derived from methyl bromide in the course of the catalytic combustion remain in the gas phase thereby avoiding any risk of dew point corrosion. In this way, cost penalties otherwise incurred through the use of scrubbing plant upstream of the expander 24 (with consequent reduction in energy available for extraction by means of the expander) or through the use of expensive materials of construction for the expander 24, are avoided.

Following energy recovery, the gas stream is processed to remove the bromine components so that any discharge to atmosphere is substantially free of such components. Such processing may for instance be effected by desuperheating the gas stream in unit 28 using water and contacting the gas stream with a suitable aqueous scrubbing media in a scrubbing section 30 to remove the $Br_2$ and HBr. HBr for instance may be removed by countercurrent contact with HBr solution and $Br_2$ may be removed by countercurrent contact with an aqueous solution of components such as sodium hydroxide, sodium carbonate, sodium bicarbonate, sodium bromide, sodium formate, sodium sulphite or mixtures containing any combination of two or more of these compounds (e.g. sodium hydroxide and sodium sulphite). The water used for desuperheating may also be employed in the scrubbing section. The cleaned gas may be discharged to atmosphere and/or used elsewhere in the production process, eg for inerting duties.

Figure 2:
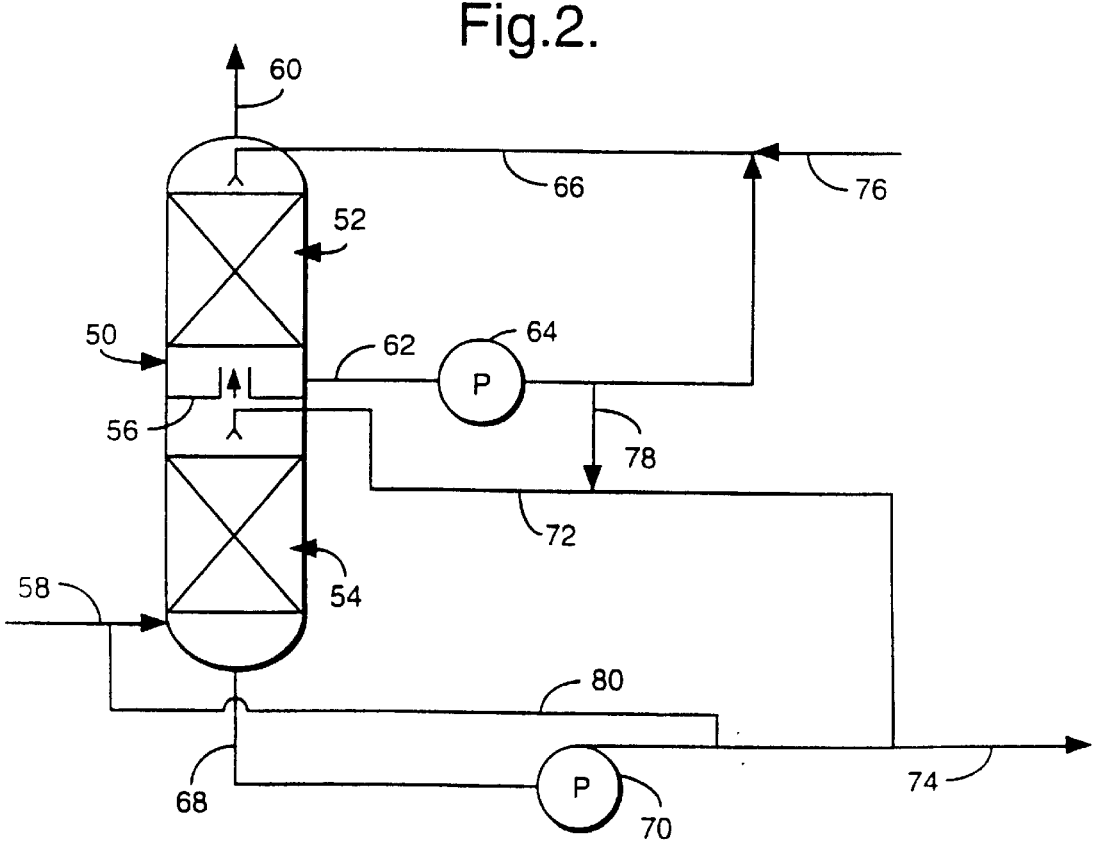
FIG. 2 illustrates a scrubbing unit for reducing the bromide/hydrogen bromide content of the effluent gas.

FIG. 2 illustrates one form of scrubbing unit 50 for use in scrubbing the effluent gas in order to achieve a bromine content in the discharged gas of less than 4 ppm vol/vol, more preferably less than 2 ppm vol/vol, with 1 ppm vol/vol being readily achievable. The unit 50 comprises a vessel having two packed sections 52 and 54. The packings employed may be any suitable type, e.g. Raschig rings, Pall rings etc. A liquid collection tray 56 is located between the two sections 52, 54. The effluent gas (together with water employed to irrigate the pipeline), following treatment to remove HBr, is fed to an inlet 58 at the base of the vessel 50 where the gas and liquid entering the vessel impinge on a plate (not shown) within the vessel base to prevent the gas/liquid mixture impinging on that part of the vessel wall opposite the inlet 58. The gas rises through the vessel, traversing the packed sections 52, 54, and leaves the vessel via outlet 60 which may be a discharge to atmosphere.

The scrubbing liquid employed may be any suitable liquid capable of removing bromine from the effluent gas, including the chemicals specified above. The scrubbing liquid is circulated around a loop including the upper section 52, exit line 62, pump 64 and inlet line 66 so that the liquid flows countercurrent to the direction of gas flow passing up through the vessel 50. A second recirculatory flow of scrubbing liquid is established in the lower part of the vessel 50, again in countercurrent relation to the gas flow, by means of outlet line 68, pump 70 and return line 72. Spent scrubbing liquid is purged from the system via line 74 and make-up liquid is supplied via line 76. The amount of scrubbing liquid pumped through the vessel per unit time will generally be far in excess of that being purged, e.g. a ratio of at least 20:1, e.g. at least 30:1 (typically of the order of 40:1). A purge line 78 interconnects the outlet of pump 64 and line 72 so that scrubbing liquid collecting in the collection tray 56 is passed to the lower recirculatory liquid flow loop. In a modification, the purge line 78 may be omitted and transfer of the scrubbing liquid from the upper section 52 to the lower section 54 and hence into the lower recirculatory loop may be implemented by allowing overflow of the liquor collecting in the tray 56. A small amount of the scrubbing liquid is routed to the inlet 58 via line 80, for example from the pump 70, in order to prevent any risk of corrosion in the region of the inlet.

In a further modification, the HBr scrubbing process may be integrated with the $Br_2$ process by incorporating a further packing section into the scrubbing tower beneath the sections 52 and 54 so that the gas stream initially passes through the HBr scrubbing section. In the HBr scrubbing section, the scrubbing liquor may be an aqueous solution of HBr flowing in a recirculatory loop as described above in relation to sections 52 and 54 with suitable purging and make-up of the loop. The HBr purge may for instance be supplied to catalyst make up.

From the foregoing, it will be seen that the bromine containing gas is subjected to a two stage scrubbing treatment allowing the bromine to be substantially completely removed before the gas is discharged from the vessel. As mentioned previously, the scrubbing liquid may be any suitable liquid for effecting bromine removal, with alkali metal compounds being preferred. Where for example the liquid is caustic soda, this is converted to sodium carbonate and bicarbonate in the scrubbing vessel as a result of absorption into the hydroxide of carbon dioxide contained in the effluent gas. Instead of, or in addition to, caustic soda, the scrubbing liquid may comprise one or more of the chemicals previously mentioned, e.g. sodium sulphite or sodium formate or other suitable reducing agent, or other compounds such as potassium hydroxide or urea.

In another aspect of the present invention, the effluent gas stream derived from the oxidation process employed in the production of an aromatic polycarboxylic acid (eg the production of terephthalic acid by the liquid phase oxidation of paraxylene), the methyl bromide containing effluent gas stream derived from the oxidation reactor is treated by means of a flameless oxidation process such as that described in any one or more of the following publications:

The Air Pollution Consultant (March/April 1993);

Paper No. 93-WP-94.06 entitled "Control of Toxic Air Emissions with a Flameless Thermal Oxidizer" (Authors: K B Woods et a) presented at the 86th Annual Meeting & Exhibition Denver, Colo. Jun. 13–18, 1993;

PCT Published Patent Applications Nos. 95/02450, 94/14008, 93/01446 and 90/12985.

U.S. Pat. Nos. 4,688,495, 4,823,711, 5,165,884 and 5,320,518.

European Published Patent Application No. 524736.

GB Patent Application No. 2182426.

This aspect of the invention may be used in conjunction with the process referred to herein in which the polycarboxylic acid is separated from the mother liquor and washed with water by means of an integrated separation and washing unit operating with superatmospheric conditions prevailing on the slurry side of the filter medium.

If necessary, in order to achieve the temperatures required for efficient destruction of the pollutant species, support fuel and air may be added to the process.

The treated gas may be used in a power recovery system, such as a gas turbine, to convert thermal energy into mechanical and/or electrical energy for use for example elsewhere in the production plant. For instance, the treated gas may be passed through an expander to convert the thermal energy into rotation of a shaft for example for driving an air compressor for supplying air to the oxidation reactor or driving an electrical generator and the treated gas may be scrubbed prior to or after passage through the energy recovery system using a scrubbing process as described herein.

We claim:

1. A process for the treatment of a high pressure effluent gas stream which contains methyl bromide from a bromine-assisted air oxidation process to remove organic constituents and recover energy, comprising (a) preheating the effluent gas stream while still at high pressure to a temperature of from 250° C. to 400° C.;

(b) catalytically oxidizing the effluent gas stream, in the optional presence of an amount of a combustion assistant selected from the group consisting of methanol, methyl acetate, hydrogen, natural gas, methane, propane, butane and mixtures thereof, to thereby raise the temperature of the oxidized gas to a value in the range of from 400° C. to 700° C. and convert methyl bromide to bromine, HBr or mixture thereof;

(c) passing the catalytically oxidized gas to an energy recovery system; and (d) thereafter recovering bromine, HBr or mixture thereof from the gas stream.

2. A process as claimed in claim 1 in which the bromine-assisted air oxidation process is a terephthalic acid process and in which the combustion assistant is methyl acetate produced as a by-assistant product in the production of said terephthalic acid.

* * * * *